United States Patent [19]

Westerberg et al.

[11] Patent Number: 4,506,872
[45] Date of Patent: Mar. 26, 1985

[54] DEVICE FOR MOUNTING ACCESSORIES ON A PATIENT SUPPORT APPARATUS

[75] Inventors: Hans Westerberg, Tyresoe; Enar Leandersson, Ekeroe, both of Sweden

[73] Assignee: Siemens Aktiengesellschaft, Berlin & Munich, Fed. Rep. of Germany

[21] Appl. No.: 523,591

[22] Filed: Aug. 16, 1983

[30] Foreign Application Priority Data

Sep. 29, 1982 [DE] Fed. Rep. of Germany ....... 3236135

[51] Int. Cl.³ ............................................. A61G 13/00
[52] U.S. Cl. ...................................... 269/322; 5/503; 378/209
[58] Field of Search ............................... 269/322–328; 378/208–209; 297/397, 399, 400; 108/90, 97, 28; 5/503, 508

[56] References Cited

U.S. PATENT DOCUMENTS

| 2,465,781 | 3/1949 | Banta | 269/328 |
| 2,713,530 | 7/1955 | Chisholm | 108/97 |
| 2,819,133 | 1/1958 | Party | 269/328 |
| 3,328,083 | 6/1967 | Bourne | 297/397 |
| 3,381,684 | 5/1968 | Anderson | 269/328 |
| 4,064,401 | 12/1977 | Marden | 269/328 |
| 4,391,438 | 7/1983 | Heffington | 269/328 |

OTHER PUBLICATIONS

Koordinat 3D–Siemens Brochure, "Ceiling Suspended Table for Angiography".

Primary Examiner—Robert C. Watson
Attorney, Agent, or Firm—Hill, Van Santen, Steadman & Simpson

[57] ABSTRACT

A device for mounting accessories for a patient support apparatus which has a frameless x-ray permeable platform. In order to be able to apply accessories in the head region of the patient and still be able to make radiographs in this region, the device includes a stirrup member having a shape which is matched to the exterior edge contour of the region of the platform for the head region, gripping members applied on lateral portions of the stirrup member and an arrangement for urging the lateral portions together to clamp the gripping members onto the edge of the platform after the device has been telescoped thereon. The device also includes at least one mounting track or rail to provide a base for mounting the accessories.

13 Claims, 3 Drawing Figures

DEVICE FOR MOUNTING ACCESSORIES ON A PATIENT SUPPORT APPARATUS

BACKGROUND OF THE INVENTION

The present invention is directed to a device for mounting accessories on a patient support apparatus which patient support apparatus comprises a frameless x-ray permeable plate.

A mounting device or arrangement which is applied to the head end of a patient support apparatus is known and an example is disclosed in the Siemens brochure KOORDINAT 3D. This mounting arrangment is employed if multi-directional radiographs, i.e., oblique radiographs from several directions, are to be made in the chest region or abdominal region. In the case of an x-ray examination, no accessories may be present in the region because they would impair the radiographs and would interfere with the handling of the apparatus. The known devices for mounting consist of a wooden plate, which has tracks and can be slipped onto an x-ray permeable plate or platform of the patient support apparatus. This mounting arrangement also possesses holes for supporting accessories such as arm supports, handles, control devices, pressure receivers and containers of sodium chloride solution.

The known mounting arrangement described hereinabove has several disadvantages, one consists in that it does not possess any standard tracks or rails for the mounting of accessories. Thus, accessories, which are designed and built for mounting on standard tracks and rails must be partially reconstructed in order that they will be able to be mounted in the holes of the device for mounting accessories. In addition, the known wooden plate extends beneath the x-ray transparent head section of the patient support apparatus so that this region cannot be radiographed in an interference-free manner when the plate of the mounting device is present.

SUMMARY OF THE INVENTION

The present invention is directed to producing a device for mounting accessories for use in a patient support apparatus which apparatus consists of an x-ray permeable plate and which apparatus has standard rails for mounting accessories with standard clamps. Moreover, the device of the present invention allows radiographs to be made in this region.

To accomplish this goal, the device for mounting accessories in accordance with the present invention comprises a stirrup member having a shape matched to the exterior edge of a region of the support platform or plate, said stirrup member surrounding this portion of the edge of the platform and having gripping means for engaging sections or portions of this edge, a rail for mounting accessories being secured on the stirrup member and clamping means for urging the gripping means into tight engagement on the edge of the platform or plate to clamp and to secure the device on the platform of the patient support apparatus.

Preferably, the stirrup member has two lateral portions which extend on opposite edges of a head portion of the x-ray permeable platform or plate and the two lateral portions are connected at one end by a rigid member which passes beneath the platform with the clamping means being positioned at the opposite end. Preferably, the clamping means is a threaded arrangement which will move the two lateral portions toward each other to clamp the engagement means which are preferably channel-shaped members onto the edge of the platform. Preferably, each rail for mounting accessories is part of the U-shaped members forming the engagement means and the position of the engagement means are such that the entire device can be easily slipped onto the head end of the platform.

DESCRIPTION OF THE PREFERRED EMBODIMENTS

Figure 3:
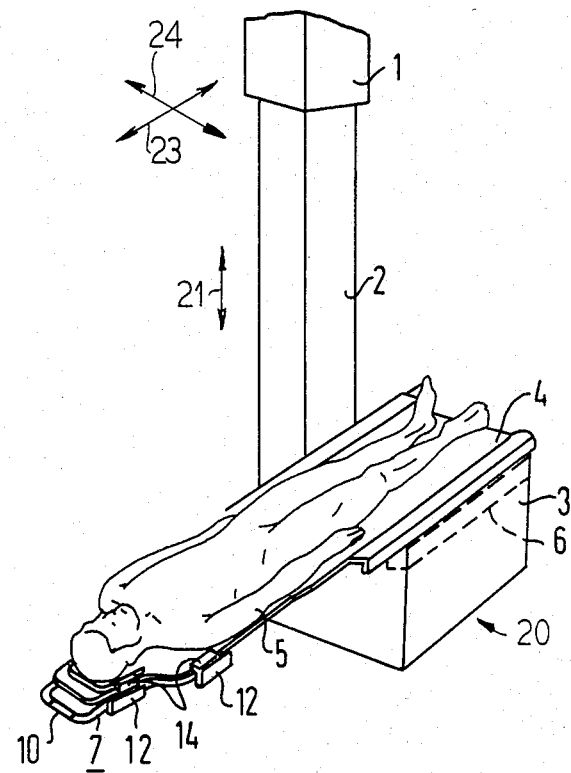
FIG. 3 is a perspective view of a patient support apparatus with the device for mounting positioned thereon.

The principles of the present invention are particularly useful when incorporated in a device 7 (FIG. 1) which is mounted on a patient support apparatus generally indicated at 20 in FIG. 3. The patient support apparatus 20 has a telescopic column 1 on which an extensible arm is vertically received for movement in the direction of arrow 21. On an end of the extensible arm 2, a support frame 3 is mounted and is provided with a patient support consisting of a frameless x-ray permeable plate or platform 4 for the patient 5. The movement of the extensible arm 2 in the column 1 will change the horizontal position of the platform 4 and any patient 5 placed thereon as indicated by the arrow 21. As is customary in the apparatus, the column 1 may be mounted on a track arrangement (not illustrated) to allow movement in horizontal directions indicated by arrows 23 and 24 relative to an x-ray device which is not illustrated.

As illustrated, the support frame 3 has beams or channels 6, which are displaceable in a longitudinal direction of the platform 4 between a stored position as illustrated and an extended position along the edge of the platform 4 for mounting of accessories. If x-rays, particularly oblique radiographs, are to be made in the region of the head or the shoulder of the patient, the beams 6 with their tracks are removed from the supporting frame and placed in the extended position so that the necessary accessories can be mounted thereon. The length of the beams and their points of mounting are selected so that radiographs will not be influenced thereby.

If multi-directional radiographs are to be made in the chest region or abdominal region of the patient 5, the beam 6 must be placed in the stored position illustrated in the drawing in FIG. 3. The known and therefore not illustrated accessories are now mounted on a standard track 12 of the device 7 which will be described in greater detail hereinafter and which device 7 is secured on the head end of the platform 4. The chest and abdomen of the patient 5 are now free of the beams 5 and accessories so that a flawless radiograph can be made at random angles.

Figure 1:
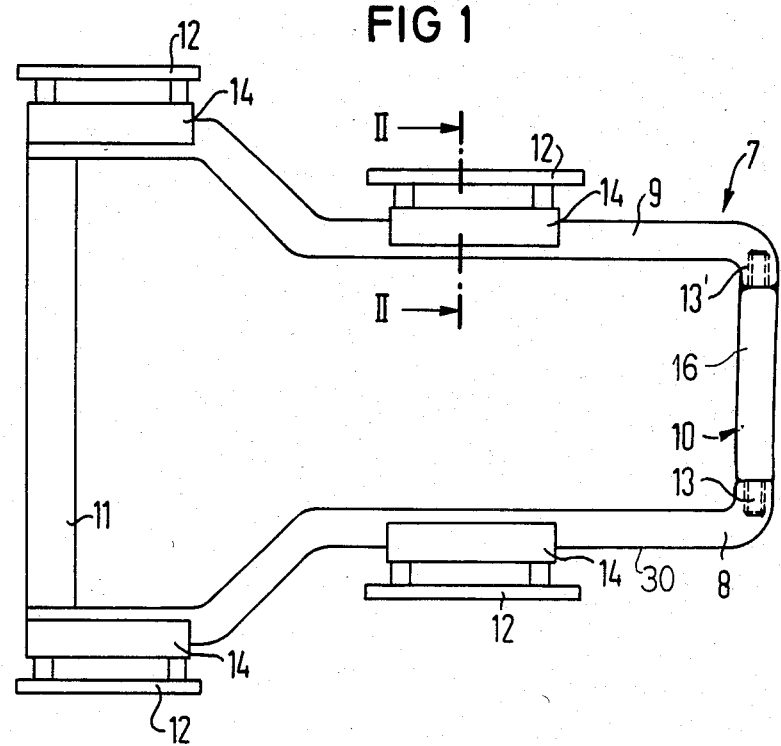
FIG. 1 is a plan view of the device in accordance with the present invention.
Figure 2:
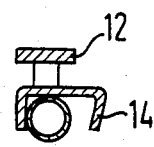
FIG. 2 is a cross-sectional view taken along the lines II—II of FIG. 1.

As best illustrated in FIGS. 1 and 2, the device 7 consists of a stirrup member 30 which is matched to the edge contour of the head region of the plate or platform 4. The stirrup exhibits two lateral parts 8 and 9 which are interconnected rigidly at one end by a clamping means 10 and at the other end by a rigid bar 11. Thus, the one end of the U-shaped stirrup member is closed by the bar 11 which is made of an x-ray permeable material. The bar 11 is mounted on the lateral portions 8 and 9 so that it may extend underneath the platform 4 and exhibits a shape which corresponds to the profile of the platform. Each of the lateral parts 8 and 9 have two parallel extending portions and an angularly extending portion and are provided with gripping means for engaging the edge of the platform which are illustrated as channel-shaped clamps 14. As best illustrated in FIG. 2, a standard track 12 is mounted on each of the channel-shaped clamps 14 and provides a base for attaching accessories.

As best illustrated, each of the lateral members 8 and 9 are formed of a tubular member which has the desired profile bent therein. In order to form the clamping means 10, a center member 16 having a structure similar to a turnbuckle is provided such as with threaded ends 13 and 13′ which are received in nuts mounted in the tubular members forming each of the elements 8 and 9. Thus, rotation of the center member 16 of the clamping means 10 in one direction such as clockwise will draw the two members 8 and 9 toward each other while rotation in the opposite direction will move them apart. It should be noted that while threaded portions 13 and 13′ are illustrated for each of the lateral parts 8 and 9 and have different right-hand and left-hand threads, one of these elements such as 13′ could be replaced by a socket connection so that only one threaded member is required.

The distance between the lateral parts 8 and 9 is so dimensioned that the stirrup member 30 can be easily slipped onto a head part of the platform 4. Upon turning of the center member 16 of the clamping means 10 which in the illustrated embodiment has threaded projections 13 and 13′ engaged in threaded sockets on the ends of parts 8 and 9, respectively, the lateral parts 8 and 9 are moved toward each other so that the channels 14 will clampingly grip the edge of the platform 4 and consequently rigidly mount the device 7 thereon. To detach the device 7, the center member 16 of the clamping means 10 is rotated in the opposite direction so that the two parts 8 and 9 are moved away from each other to release the gripping of the channels 14 on the edge of the platform.

The shape of the mounting arrangement leaves the region of the x-ray permeable platform 4 which is spanned by the stirrup member 30 free of material which would interfere with the radiograph. Consequently, when the device 7 is mounted on the platform 4, radiographs can be made in a trouble-free fashion in the regions of either the shoulders or the head.

Although various minor modifications may be suggested by those versed in the art, it should be understood that we wish to embody within the scope of the patent granted hereon, all such modifications as reasonably and properly come within the scope of our contribution to the art.

We claim:

1. A device for mounting accessories for a patient supporting apparatus having a frameless, x-ray permeable platform, said device comprising a stirrup member having two lateral portions and having a shape matched to the exterior edge contour of a region of the platform to surround said region, said stirrup member having gripping means for engaging a portion of the edge of the platform, said stirrup having at least one mounting track for providing a mounting base for accessories and having clamping means for connecting the lateral portions together and for urging the gripping means into tight engagement on the edge of the platform when the device is assembled on the platform.

2. A device according to claim 1, wherein the stirrup member at one end has a continuation forming a rigid connection between the two lateral portions thereof.

3. A device according to claim 1, wherein the clamping means includes a threaded fastener received in a nut.

4. A device according to claim 1, wherein the gripping means comprise channel members disposed on the stirrup member.

5. A device according to claim 1, wherein said clamp means is positioned at one end of the two lateral portions.

6. A device according to claim 5, wherein the stirrup member includes a bar member rigidly interconnecting the two portions at an end opposite said clamping means, said bar member being constructed of an x-ray permeable material and extending beneath the platform when the device is mounted thereon.

7. A device according to claim 6, wherein the bar member has a profile matched to the shape of the platform profile.

8. A device for mounting accessories for a patient supporting apparatus having a frameless, x-ray permeable platform, said device for mounting comprising a stirrup member having a shape matched to the exterior edge contour of a region of the platform to surround said region, said stirrup member having gripping means for engaging a portion of the edge of the platform and including a bar member positioned at one end and extending underneath the platform, said bar member consisting of an x-ray permeable material, said stirrup member having at least one mounting track for providing a mounting base for accessories and having clamping means for urging the gripping means into tight engagement on the edge of the platform when the device for mounting is assembled on the platform.

9. A device according to claim 8, wherein the bar member has a shape which is matched to the profile of the platform.

10. A device for mounting accessories for a patient supporting apparatus having a frameless, x-ray permeable platform, said device comprising a stirrup member having a shape matched to the exterior edge contour of a region of the platform to surround said region, said stirrup member having gripping means for engaging a portion of the edge of the platform, said stirrup member having at least one mounting track for providing a mounting base for accessories and having clamping means for urging the gripping means into tight engagement on the edge of the platform when the device is assembled on the platform, said stirrup member including two lateral portions interconnected at one end by a rigid connection and at the opposite end by the clamping means, said clamping means comprising at least one threaded nut received on an end of one of said lateral portions, and a threaded fastener mounted for rotation relative to the other of said portions and being threaaded in said nut.

11. A device according to claim 10, wherein the means for gripping comprise channel-shaped members disposed on the lateral portions.

12. A device according to claim 11, wherein each of the channel members are provided with a mounting track for providing the mounting base for accessories.

13. A device according to claim 1, wherein the two lateral portions are interconnected at one end by a rigid connection and at the opposite end by the clamping means, said clamping means comprising a center member with a right-handed threaded portion at one end and a left-handed threaded portion at the other end and a pair of complementary threaded nuts secured to the lateral portions so that rotation of the center member in one direction causes spreading of said portions and rotation in the opposite direction causes the two portions to move toward each other.

* * * * *